US006699702B1

(12) United States Patent
Patel et al.

(10) Patent No.: US 6,699,702 B1
(45) Date of Patent: Mar. 2, 2004

(54) PROKARYOTIC SYSTEM DESIGNED TO MONITOR PROTEASE ACTIVITY

(75) Inventors: Pramathesh Patel, Thorndale, PA (US); David Lach, Andalusia, PA (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/478,631

(22) Filed: Jan. 6, 2000

Related U.S. Application Data (60) Provisional application No. 60/115,270, filed on Jan. 8, 1999.

(51) Int. Cl.[7] .................. C12N 15/00; C12N 15/09; C12N 15/64; C12Q 1/68; C07H 21/04
(52) U.S. Cl. ............... 435/252.3; 435/23; 435/91.4; 435/320.1; 435/69.7; 435/69.1; 435/252.33; 435/6; 435/7.2; 435/7.37; 435/7.4; 435/24.3; 536/23.1; 536/23.4; 536/24.1; 530/350
(58) Field of Search ............... 435/6, 7, 2, 7.37, 435/7.4, 23, 24, 320.1, 91.4, 252.33, 69.1, 69.7, 252.3; 530/350; 536/23.4, 24.1, 23.1

(56) References Cited

U.S. PATENT DOCUMENTS 5,891,635 A 4/1999 Dasmahapatra

OTHER PUBLICATIONS

Sices, et al. Proc. Natl. Acad. Sci. USA, Mar. 1998, vol. 95, pp. 2828–2833.*
Hilliard, et al. The Journal of Biological Chemistry. vol. 273, No. 1, pp. 524–527, Jan. 1998*
Lawler et al. (1999) Analytical Biochem, 269:1:133–138.
Dasmahapatra et al. (1992) Proc. Natl. Academy of Sciences, 89:4159–4162.
Fields et al. (1994) Trends in Genetics, 10:8:286–292.
Liebig et al. (1991) Proc. Natl Academy of Sciences, 88:14:5979–5983.
Nduwimana et al. (1995) Annual Biol. Clinl 53:251–264.
Melnick (1985) Virology, Raven Press, New York, pp. 739–794.
Ratner et al. (1985) Nature 313:277–283.
Farmerie et al. (1987) Science 236:305–308.
Imai et al. (1986) J. Biochem. 100:425–432.
Cox et al. (1988) Am. Rev. Respir. Dis. 137:371–375.
Albin et al. (1987) Am. Rev. Respir. Dis. 135:1281–1285.
Toyoda et al. (1986) Cell 45:761.
Hanecak et al. (1984) 37:1063.
Kohl et al. (1988) Proc. Natl. Acad. Sci. 85:4686–4690.
Billich et al. (1988) J. Biol. Chem. 263:17905–17908.
Moore et al. (1989) Biochem. Biophys. Res. Commun. 159:420–425.
Blumenstein et al. (1989) Biochem. Biophys. Res. Commun. 163:980–987.
Dreyer et al. (1989) Proc. Natl. Acad. Sci. 86:9752–9756.
Krausslich et al. (1989) Proc. Natl. Acad. Sci. 86:807–811.
Darke et al. (1988) Biochem. Biophys. Res. Commun. 156:297–303.
Baum et al. (1990) Proc. Natl. Acad. Sci. 87:10023–10027.
Block et al. (1990) Antimicro. Ag. Chemo 34:2337–2341.
Black et al. (1997) Nature 385:729–733.
Kezdy et al. (1970) Methods in Enzymology 19:3–20.
Knight (1995) Methods in Enzymology 248:18–34.
Baumeister et al. (1992) J. Mol. Biol. 226:1257–1270.
Meffert et al. (1990) Nucl. Acids Res. 22:6633–6636.
Berens et al. (1992) J. Biol. Chem. 267:1945–1952.
Skerra (1994) Gene 151:131–135.
Murray et al. (1993) Gene 134:123–128.

* cited by examiner

*Primary Examiner*—Gerald G. Leffers, Jr.
(74) *Attorney, Agent, or Firm*—Audrey F. Sher (57) ABSTRACT

The invention relates to a prokaryotic cell system for monitoring protease activity. The invention also includes assays for identifying protease inhibitors and protease modulators, determining the amino acid sequence of a protease cleavage site for a known protease, identifying and cloning a protease whose cleavage site is known, and rapidly identifying a form of a protease exhibiting increased activity relative to a control protease.

24 Claims, 8 Drawing Sheets

(1 of 8 Drawing Sheet(s) Filed in Color)

Forward oligo:

PstI                            Not I 5'--- cggc*ctgcag* cgagtcgggg ccct*gcgcggccgc*tnnbnnb                         AscI nnbnnbnnbn nbnnb*ggcgc gcc*taata ggatcccccg                  HindIII accggccggc c*aagctt*ccg gc---3'

---

Reverse oligo:

HindIII                        AscI 5'--- gcgg*aagct* tggccggccg gtcgggggat cctatta*ggc*

NotI

*gcgcc*vnnvn nvnnvnnvnn vnnvnna*gcg* gccgcgcagg

PstI gccccgactc g*ctgca*ggcc g---3'

FIG. 6

| | Inducer for protease | 60 ug.well Cm | 120 ug/well Cm | 20 ug/well Rifampicin |
|---|---|---|---|---|
| Repressor (wild type) "" "" "" | --- | 20 | 22 | 23 |
| | +++ | 21 | 23 | 22 |
| Repressor (with cleavage site) "" "" "" | --- | 18 | 20 | 24 |
| | +++ | 10 | 11 | 24 |

PROKARYOTIC SYSTEM DESIGNED TO MONITOR PROTEASE ACTIVITY

This application claims priority from provisional U.S. Application Serial No. 60/115,270, filed Jan. 8, 1999, which is incorporated herein by reference in its entirety.

FIELD OF THE INVENTION

This invention relates to a prokaryotic cell system and cell based assays for: identification of protease inhibitors and protease modulators; ii) determination of the amino acid sequence of a cleavage site for a known protease; iii) identification and cloning of a protease whose cleavage site is known; and iv) rapid identification of a form of a protease that exhibits increased protease activity relative to a control protease.

BACKGROUND OF THE INVENTION

Proteases are enzymes that cleave peptide bonds, and hence by definition, alter proteins. These enzymes are broadly classified into four groups: a) serine proteases, b) cysteine proteases, c) aspartate proteases and d) metalloproteases (Nduwimana et al., Ann. Biol. Clin. 53:251–264 (1995). This classification is primarily based on the mechanism of action. Many of these proteases which cleave peptide bonds at specific sites have been implicated in a variety of human diseases (Melnick, J. L., in Virology 1985, B. N. Fields, Ed. Raven Press, New York, pp. 739–794; Ratner et al., Nature (1985) 313:277–283; Farmerie et al., Science (1987) 236:305–308; Imai, T., et al., J. Biochem. (1986) 100:425–432; Cox, D. W. et al., Am. Rev. Respir. Dis., (1988) 137:371–375, Albin, R. J. et al., Am. Rev. Respir. Dis., (1987) 135:1281–1285) These diseases include hypertension, onset of emphysema, several neurological disorders, onset of respiratory diseases and several autoimmune diseases. Proteases have also been shown to play a very important role in the physiology of several pathogenic microorganisms and the maturation of viruses (Toyoda et al., Cell (1986) 45:761., Hanecak et al., Cell (1984) 37:1063; Kohl, N. E., et. al., Proc. Nat. Acad. Sci. (USA) (1988) 85:4686–4690)) Hence, proteases are also implicated in the establishment of infectious diseases.

In all of these cases, it is believed that a specific inhibitor or a modulator of a specific protease may serve as a therapeutic agent that can be used to either prevent a disease or help control and mitigate the adverse effects of a disease. This has led to an enormous effort to discover these specific protease inhibitory agents or agents that help modulate protease activity. Conventional methods in the past have used kinetic enzyme assays that monitor the cleavage of either a radiolabeled substrate or a chromogenic substrate (Billich, S., et al., J. Biol. Chem., (1988) 263:17905–17908, Moore, M. L., et. al. Biochem. Biophys. Res. Commun. (1989) 159:420–425; Blumenstein J. J., et al., Biochem. Biophys. Res. Commun. (1989) 163:980–987;). Other methods have also been used to monitor protease activity, however, all of these techniques are time consuming, cumbersome and labor intensive (Dreyer G. B. et al. Proc. Nat. Acad Sci. (USA) (1989) 86: 9752–9756; Krausslich, H. et al. Proc. Natl. Acad. Sci. (USA) (1989) 86: 807–811; Drake, P. L., et al., Biochem. Biophys. Res. Commun. (1988) 156:297–303). None of these methods could be used in a high throughput format to evaluate millions of compounds that can be generated using automated combinatorial chemistry. More recently, whole cell based enzyme assays have been developed by engineering a cleavage site within the structural portion of a particular enzyme or an efflux pump (Baum, E. Z. et al., (1990) Proc. Natl. Acad. Sci. (USA) (1990) 87:10023–10027; Block, T. M. et al., Antimicro. Ag. Chemo. (1990) 34:2337–2341). These assays are more compatible with high throughput screening, however they are not sensitive and versatile. It has long been realized that a robust, versatile and sensitive assay that can be used in a homogenous format and is compatible with high-throughput screening would be highly beneficial in the effort to identify inhibitors and modulators of protease activity.

In many of the disease cases mentioned above it has long been established that a specific protease activity is implicated (Black, R. A., et al., Nature (1997) 385:729733). However, the protease gene has not been cloned. A rapid and reliable method has been needed to screen a genomic or cDNA library to clone the protease. Conventional molecular biological techniques have been used in the past with some degree of success. Also, in many cases the specific cleavage sequence of a particular protease is not known. At the present time a rapid and reliable method is not available to screen a library of protease cleavage sites (WO 96/21009).

Finally, in the field of protein structural studies there has always been a need for generating large quantities of the protein being studied. Heterologous gene expression systems utilizing the bacteria *Escherichia coli* (*E. coli*), or the yeast *Picchia pastoris* or the insect virus Bacculovirus have been widely used. Unfortunately, in very many cases the heterologous protein is found to be sequestered in insoluble aggregates called inclusion bodies or is found in some other precipitated or aggregated inactive form. In many cases, a slight change in the amino acid sequence of the protein results in the production of a soluble and hence active protein. The change is subtle enough so that the integral structure or the activity of the protein remains unaffected. However, identification of these subtle solubilizing changes is often very cumbersome and labor intensive. A rapid method has long been sought to screen a library of mutant proteases and identify the ones that are expressed in a more soluble and hence active form.

SUMMARY OF THE INVENTION

The present invention relates to a prokaryotic cell system for monitoring protease activity that can be used to i) identify protease inhibitors and protease modulators, ii) determine the sequence of a protease cleavage site for a known protease, iii) identify and clone the gene for a protease whose cleavage site is known, and iv) rapidly identify a form of a protease that exhibits protease activity when the wild type protease exhibited little or no activity in a prokaryotic system.

One aspect of the invention is a prokaryotic cell system for monitoring protease activity comprising a prokaryotic cell comprising:
a) a gene coding for a protease;
b) a modified DNA-binding repressor gene wherein said modification is one or more cognate cleavage sites of the protease engineered into one or more exposed and permissive loops of the repressor polypeptide encoded by said repressor gene; and
c) a reporter cartridge wherein the expression of the reporter gene in said reporter cartridge is regulated by a promoter whose transcription can be negatively regulated by the wild type or the modified DNA-binding repressor protein.

Using this system, the activity of a protease can be determined by monitoring the level of expression of the reporter gene; i.e., the reporter gene activity. The modified or the wild-type repressor negatively regulates the expression of the reporter gene. If the protease is expressed in the same cell and is active, it cleaves the modified repressor at its cognate cleavage site, which has been engineered into the repressor. The cleaved repressor is not able to bind to its cognate DNA sequence and hence does not regulate the expression of the reporter gene. Thus by monitoring the activity of the reporter gene, we can monitor the activity of the protease.

Another aspect of the invention is an assay for identifying protease inhibitors and protease modulators. This can be achieved by using the above mentioned prokaryotic cell system capable of expressing a protease, a modified DNA-binding repressor containing the cognate cleavage site, and the appropriate reporter cartridge. The cell can be grown in the presence of a potential inhibitor or potential modulator. Upon incubation and allowing for the expression of the protease, transcription of the reporter gene can be quantified. The level of expression can be used to correlate to the efficacy of the potential protease inhibitor or potential protease modulator.

Another aspect of the invention is an assay to determine a cleavage site of a known protease whose cleavage site is not known. This can be achieved, for instance, in the following way. A random library of modified repressors can be constructed. The modification is achieved by engineering a random DNA sequence in the region coding for a permissive and exposed loop of the repressor. The DNA sequence could code for extra amino acids in the exposed and permissive loop. During the design of the library, care should be taken to maintain the reading frame of the repressor polypeptide. Once the library of plasmids coding for the modified repressors is constructed, it is transformed into an appropriate host strain, which has the reporter cartridge, as well as a plasmid that expresses the specific protease. Cells that have the plasmid coding for the modified repressor with the appropriate cleavage site engineered will have a higher level of expression of the reporter gene. These cells can be identified and isolated. The plasmids from those cells can be isolated, sequenced and the cleavage site determined.

Another aspect of the invention is an assay to identify and clone the gene coding for a protease site whose cleavage site is known. This can be achieved, for instance, in the following way. A genomic DNA or cDNA library can be constructed using the organism from which the gene coding for the protease has to be identified. The library is transformed into an appropriate host strain, which has the reporter cartridge, as well as a plasmid that codes for a modified repressor which has the cleavage site engineered into an exposed and permissive loop. Again, cells that have the plasmid which codes for the cognate protease activity will have a higher level of expression of the reporter gene. The plasmid from these cells can be isolated and characterized to reveal the gene that codes for a protease.

Another aspect of the invention is an assay to rapidly identify a form of a protease, such as a mutant or a naturally-occurring protease variant, that exhibits increased protease activity relative to a control protease. A mutant protease may be useful when the wild type has been found to exhibit little or no activity in a prokaryotic system. This can be achieved, for instance, in the following way. A randomly mutagenised library of the protease can be generated. The library is transformed into an appropriate host strain, which has the reporter cartridge as well as a plasmid that codes for a modified repressor which has the cleavage site engineered into an exposed and permissive loop. Again, cells that express a more soluble protease will have a higher level of expression of the reporter gene. The plasmid, and hence the protease gene mutant, can be isolated from these cells and characterized.

Another aspect of the invention is a method of inhibiting or modulating a protease by contacting said protease with a protease inhibitor or protease modulator first identified to be a protease inhibitor or protease modulator by a method of the invention.

Another aspect of the invention is a method of cleaving a peptide bond comprising contacting said peptide bond with an effective amount of a protease encoded by the nucleotide sequence first identified to encode a protease by a method of the invention.

Another aspect of the invention is a method of cleaving a peptide bond comprising contacting said peptide bond with an effective amount of a protease first identified to exhibit increased protease activity relative to a control protease by a method of the invention.

DESCRIPTION OF FIGURES

The patent or application file contains at least one drawing executed in color. Copies of this patent or patent application publication with color drawing(s) will be provided by the Office upon request and payment of the necessary fee.

FIG. 2 is a schematic representation of the modification of the tetracycline repressor coding region. It illustrates the insertion of the hCMV protease cleavage site (SEQ ID NO:2) in between helix 4 and helix 5 (SEQ ID NO. 1). It also illustrates the insertion of the hCMV protease cleavage site (SEQ ID NO:4) in between helix 8 and 9 (SEQ ID NO:3) of the tetracycline repressor. The hCMV protease cleavage sequence is boxed. The additional amino acids have been inserted to accommodate the engineering of the NotI and AscI restriction enzyme sites.

FIG. 3 is a schematic representation of the reporter cartridge used in the examples described. It illustrates the relative position of the tetracycline repressor binding site (Tet-RE) in comparison with the cannonical −35, −10 and the +1 regions of a typical $E.$ $coli$ promoter. It also shows the relative positioning of the bacterial ribosomal binding site (rbs) and the reporter gene. Relative positions of convenient and useful restriction enzyme sites are also shown.

FIG. 4 shows an electronically scanned image of plates used to demonstrate the proof of principle of the assay. The dark (orange) area represents growth. The light (yellow) area represents area of no growth. As described in detail in the text below, $E.$ $coli$ cells containing both the reporter and the test expression plasmids were seeded in LB agar containing the appropriate antibiotics. As indicated above the plates, IsoPropyl Thio-galactopyranoside (IPTG) was either included or not included in the medium. Six microliters of either chloramphenicol (Cm) (60 ug/ml) or rifampicin (Rif) (30 ug/ml) was added to the plates as indicated. The plates were incubated and then the effect of chloramphenicol on the growth was observed. Rifampicin was included as a control.

FIG. 5 is a schematic representation of the expression plasmid used in the examples. The detailed construction of the plasmid is as described in the text below. The relative positions of the origin of replication (ori), The T7 promoter (T7), the hCMV protease gene (CMV protease), the b-lactamase gene (ampR), the tetracycline repressor (Tet-R*) and the gene coding for the lac operon repressor (lacI) gene is as shown.

FIG. 8 is a diagram of the bacterial selection scheme for obtaining soluble HCV protease mutants. See Example 4 for a detailed description of the system. (Center) expression plasmid (expressing HCV NS4a-NS3 fusion protease and modified Tet repressor) and chromosomally encoded Tet promoter-CAT (chloramphenicol acetyl transferase) gene fusion; (Right) case if NS3 protease is insoluble (activity masked by insolubility of the protease resulting in chloramphenicol-sensitive bacteria); (Left) case if NS3 protease is soluble (protease is active resulting in chloramphenicol-resistant bacteria).

FIG. 9 is SDS-PAGE analysis of expression of various HCV NS4a-NS3 fusion protein constructs. Plasmid containing cells were grown to $OD_{600}$–0.7 and 10 ml cultures were induced with 0.25 mM IPTG for 20 hours at 20 degrees C. Cells were harvested by centrifugation (1500 rfc) in a tabletop microfuge and cell pellets were resuspended in 1 ml of 25 mM Na-phosphate buffer,pH 7.5; 0.5M NaCl, 2 mM DTT, 10M ZnCl, 10 mM MgCl, 10 g/ml DNAse and sonicated twice for 1 min at power 5 in pulse mode. The homogenates were spun down in tabletop microfuge at max speed (20800 rfc) for 20 min. Homogenates and supernatants were analyzed on 10–20% SDS-PAGE pre-cast gels (Bio-Rad). Lane 1, molecular weight standards. The following samples are in pairs of homogenate and supernatant, respectively: Lanes 2 & 3, mutant HCV NS4a-NS3 fusion protease; Lanes 4 & 5, mutant HCV NS4a-NS3 fusion protease.

DESCRIPTION OF THE INVENTION

The following definitions are provided to more clearly delineate what is contemplated in this invention.

The term prokaryotic host cell includes, but is not limited to, such genera and species as:

*Escherichia coli*
Salmonella
Klebsiella
Pseudomonas
Caulobacter
Rhizobium and the like.

The term protease refers to a polypeptide that can cleave an amide linkage in a polypeptide. The gene coding for a protease refers to a DNA sequence that codes for the entire protease polypeptide or a segment of the protease that can cleave an amide linkage in a polypeptide chain.

The term repressor refers to a polypeptide or a segment of the polypeptide that can bind to a specific DNA sequence. The binding of the repressor protein to its cognate DNA sequence represses the transcription from a specific promoter. This promoter is deemed to be negatively regulated by the repressor protein.

The term modification of the repressor refers to engineering the DNA sequence coding for the repressor in such a manner that it includes additional amino acid residues that could code for a specific protease cleavage site. The term exposed and permissive region of the repressor means the following. Permissive refers to engineering of the above mentioned additional amino acids in the repressor coding region in such a manner that just the insertion of the extra amino acids does not prevent the binding of the repressor to its cognate DNA sequence. Exposed refers to the fact that the insertion has to be in a region that is accessible to be cleaved by the protease and that the DNA binding property is destroyed upon cleavage.

The term reporter gene refers to a DNA sequence that codes for a protein or a segment of a protein whose activity can be monitored easily. These include, but are not limited to, reporter genes viz. chloramphenicol acetyl transferase, b-galactosidase, alkaline phosphatase, green fluorescent protein, other genes that confer antibiotic resistance or toxic genes that can act as suicide genes.

The term reporter cartridge refers to a unit consisting of: a promoter whose transcription activity is negatively regulated by the repressor protein; a reporter gene; and the required transcription and translational signals. The reporter cartridge can be maintained inside a cell as part of a plasmid or bacteriophage or independently replicating episome, or can be part of the host cell chromosome. To transfer the reporter cartridge onto the host cell chromosome one of several alternative procedures can be used: i) the use of a plasmid containing a temperature sensitive origin of replication can be utilized; ii) homologous recombination at the attP site of the *E. coli* chromosome; or iii) transformation using linear DNA can also be utilized.

The phrase "first identified to" refers to something which was not previously known to have the properties thereinafter described.

All of the components described herein can be synthesized or assembled using standard molecular biological methods that can be found in, for example, "Molecular Cloning, A Laboratory Manual" ($2^{nd}$ edition, Sambrook, Fritch and Maniatis 1989, Cold Spring Harbor Press). These include but not limited to: construction of recombinant expression vectors using appropriate restriction enzymes; isolation of DNA fragments; ligation of DNA fragments; generation of suitable restriction enzyme cleavage sites; modifying pieces of DNA using site directed mutagenesis; obtaining DNA fragments through chemical synthesis or by using PCR.

The source of the protease and the repressor gene can be a previously identified and cloned copy or can be obtained using genomic or cDNA libraries. The protease gene and/or the modified repressor gene can be maintained in the host cell either as part of a plasmid or bacteriophage or autonomously replicating episome, or can be part of the host cell chromosome. Preferably, the transcription of the protease gene can be regulated by an inducible promoter viz. the isopropyl thio-galacto pyranoside (IPTG) regulated lac promoter, or the thermally regulated phage promoter or any other regulated promoter. It is preferred, however not necessary, that the transcription of the repressor gene is constitutively active.

The DNA sequence coding for the protease cleavage site can be either obtained using chemical synthesis or PCR or can be cloned out of a protease substrate using standard recombinant DNA methods. The DNA sequence coding for the protease cleavage site can be engineered into the coding frame of the DNA sequence of the repressor using restriction enzyme digestion followed by ligation. If required, appropriate restriction enzyme sites can be engineered in the DNA sequence of the repressor as well as flanking the DNA sequence coding for the protease cleavage site using site directed mutagenesis or similar procedures. Additional DNA sequence coding for amino acids that may help the cleavage site become more accessible to the protease can also be added on either side of the DNA sequence coding for the protease cleavage site. It is important that the DNA sequence coding for the protease cleavage site be engineered in a region of the repressor molecule that does not destroy its DNA binding activity to its cognate DNA sequence yet is accessible to the protease.

The transcription activity of the promoter in the reporter cartridge may be measured using standard procedures. For example, biologically active proteins such as gene products conferring antibiotic resistance can be measured as a growth/no growth phenotype in the presence of the appropriate concentration of the antibiotic. Biologically active enzymes such as b-galactosidase or an anabolic enzyme can also be monitored under appropriate conditions. Enzyme activity such as alkaline phosphatase activity can be monitored by incorporating the appropriate substrate in the growth medium.

It is understood that the cloning and expression vectors used in this invention can contain one or more marker activities that can be used to select for desired transformants, such as antibiotic resistance. It is also understood that sequence(s) of DNA may be inserted in a cloning vehicle or a specific gene to assist in the transcription and translation of the desired gene and/or maintain the appropriate reading frame.

Conditions for inhibiting or modulating a protease by contacting the protease with an effective amount of a protease inhibitor or protease modulator can be determined by one of skill in the art using standard techniques as found in, for example, Kezdy, F. S. and Kaiser, E. T., *Methods in Enzymology*, (1970) 19, 3–20. Conditions for monitoring cleavage of a peptide bond by contacting the peptide bond with an effective amount of a protease can be determined by one of skill in the art using standard techniques as found in, for example, Knight, C. G., *Methods in Enzymology*, (1995) 248 18–34.

The following examples explain how to make some embodiments of this invention. From these Examples, the Detailed Description of the Invention, and the references cited therein, one of ordinary skill in the art can readily discern how to make and use these and other embodiments of the invention. The Examples are not meant to limit the scope of the invention; the scope of the invention is delineated by the claims. All references cited herein are incorporated by reference.

EXAMPLE 1

Figure 1:
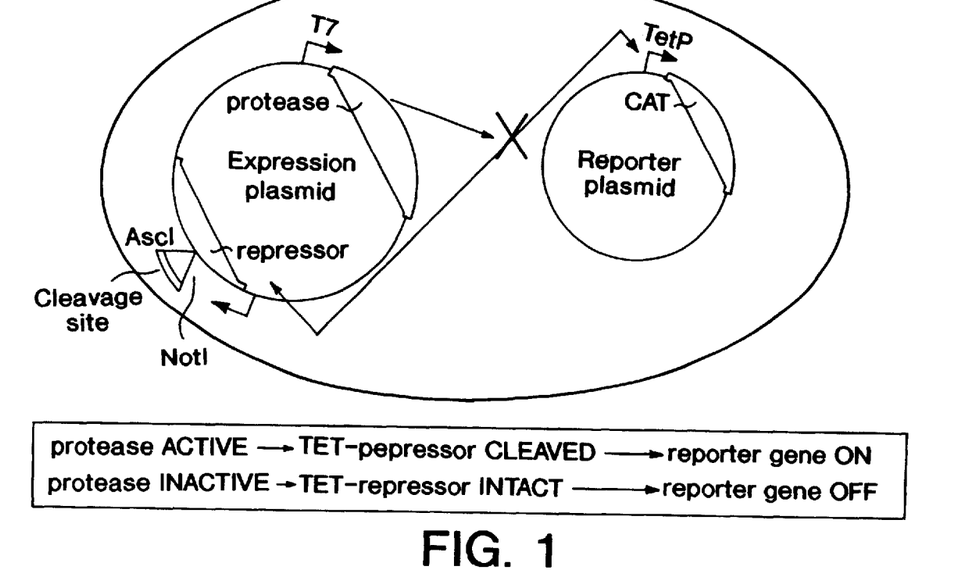
FIG. 1 is a schematic representation of the screening organism used in Example 1.

This is an example of use of the assay to screen for inhibitors of the human cytomegalovirus (hCMV) protease. A schematic representation of the screening organism is as shown in FIG. 1. The repressor used in this example was the tetracycline repressor. It belongs to a class of repressor molecules that occur in some prokaryotes in nature as a homo-dimer with an alpha helix-turn alpha helix motif and binds to a palindromic DNA sequence:

5'---C-X-C-T-A-T-C-A-X-T-G-A-T-A-G-X-G--3'   (SEQ ID NO:7)

The wild type tetracycline repressor (type B) is 207 amino acids long and binds to DNA as a dimer. Each monomer consists of 10 alpha helical coils. The intervening region between these 10 alpha helical coils exists as partially folded beta-sheets. The dimer is clearly divided into the protein core and two DNA-binding domains that are formed for each monomer, by the three-helix bundles, A1, A2 and A3. Each DNA binding domain is connected to the core by the alpha helix 4. The core helices five to ten are responsible for the dimer formation (Braumeister R., et al., J. Mol. Biol. (1992) 226:1257–1270; Meffert, R. et al., Nuc. Acids Res. (1990) 22:6633–6636, Berens, C., et al., J. Biol. Chem. (1992) 267:1945–1952; Skerra, A., Gene (1994) 151:131–135)

The hCMV protease cleavage site (-A-G-V-V-N-A-S-C-R-L-G-A-) (SEQ ID NO:8) was incorporated in between the amino acid proline (residue # 69) and glycine (residue #72). To make the cleavage site more accessible to the protease, two alanine residues were inserted in front of the sequence and a proline is inserted at the end of the sequence. To ensure complete cleavage of the repressor, a second cleavage site is inserted between helix #8 and helix #9. The above mentioned cleavage sequence is inserted between lysine (residue # 155) and proline (residue #161). Again, two alanine residues were incorporated in front of the sequence to make it more accessible to the protease. As mentioned above, the modified tetracycline repressor gene is maintained on a colE1 plasmid and is transcribed from a constitutive promoter.

The gene coding for the hCMV protease is maintained on the same plasmid as the tetracycline repressor gene and its transcription is regulated from an inducible T7 promoter.

Figure 2:
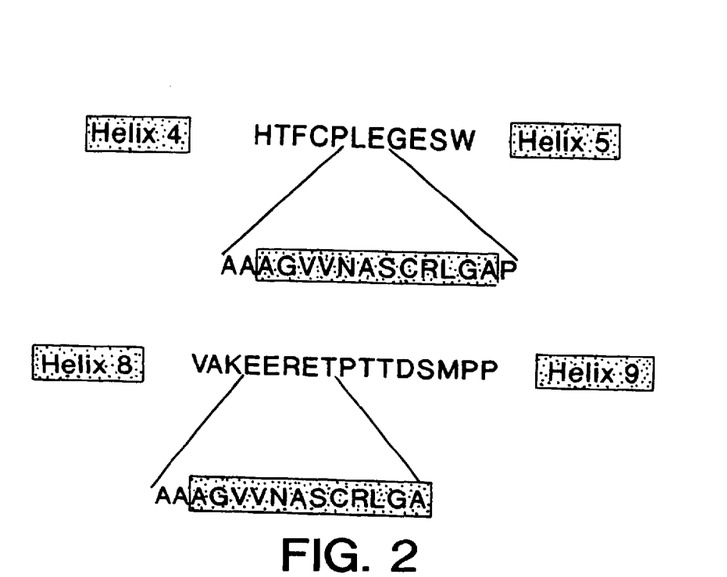
Figure 3:
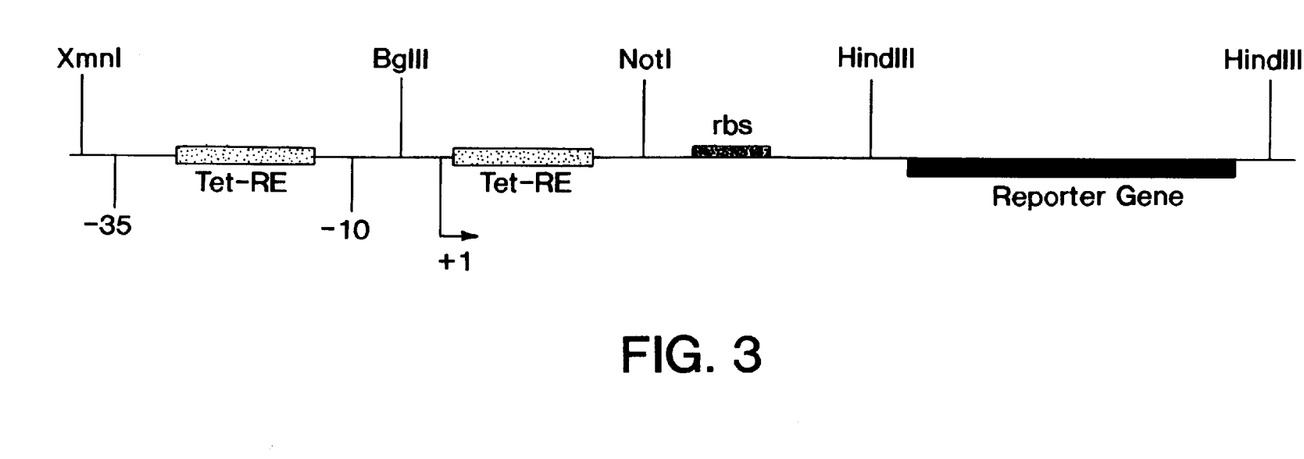

The reporter module used is the chloramphenicol acetyl transferase (CAT) gene whose transcription is regulated by a modified tetracycline repressor. A schematic representation of the modified tetracycline promoter is as shown in the FIG. 2. The promoter includes a canonical −35 region of the *E. coli* promoter followed by a tetracycline repressor binding sequence followed by a canonical −10 region of the *E. coli* promoter, the +1 transcription initiation site and then followed by another tetracycline repressor binding site. The exact DNA sequence of the modified tetracycline promoter/operator is as shown in FIG. 3. The chloramphenicol acetyl transferase gene was obtained as a cartridge from Pharmacia-Biotech.

Figure 4:
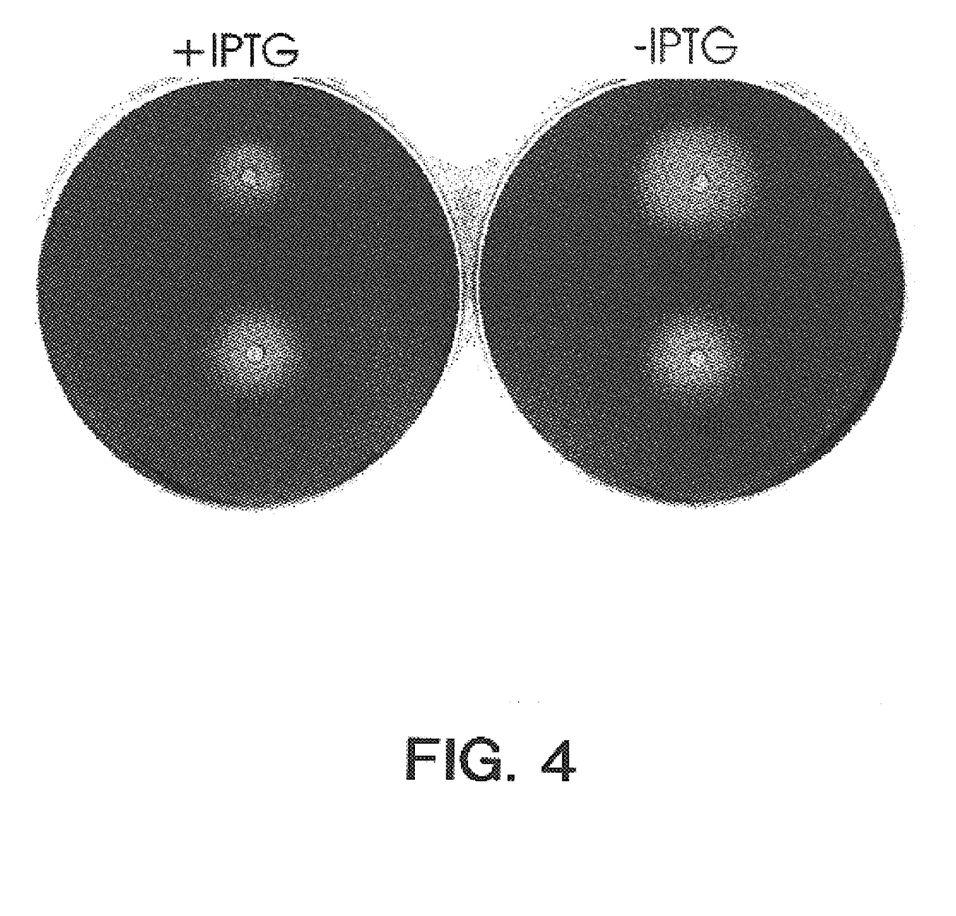
Figure 7:
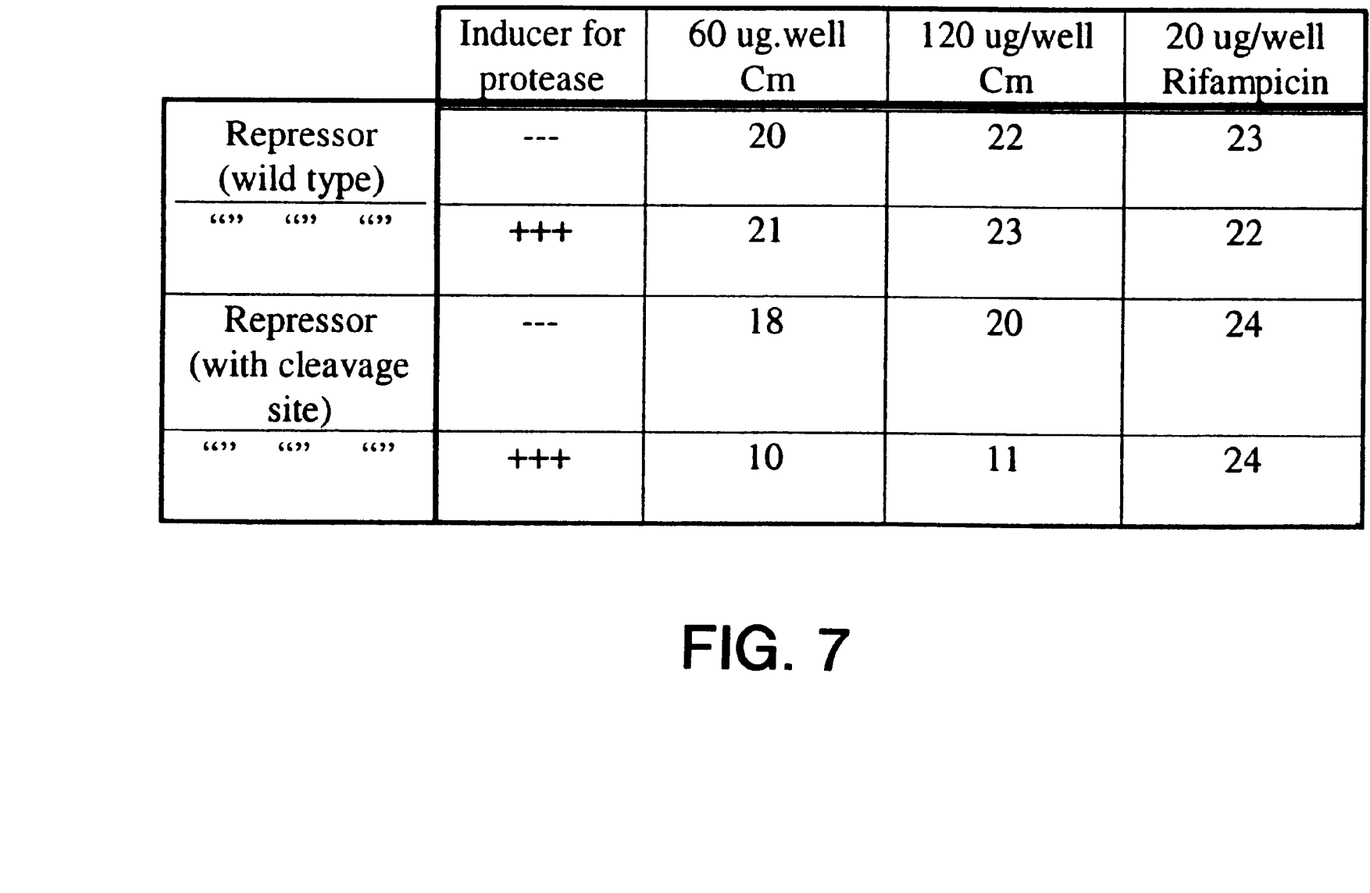
FIG. 7 is a table showing the effect of chloramphenicol on the growth of the *E. coli* test strain in the presence and absence of IPTG. The numbers represent the zone of growth inhibition as measured in mm.
Figure 8:
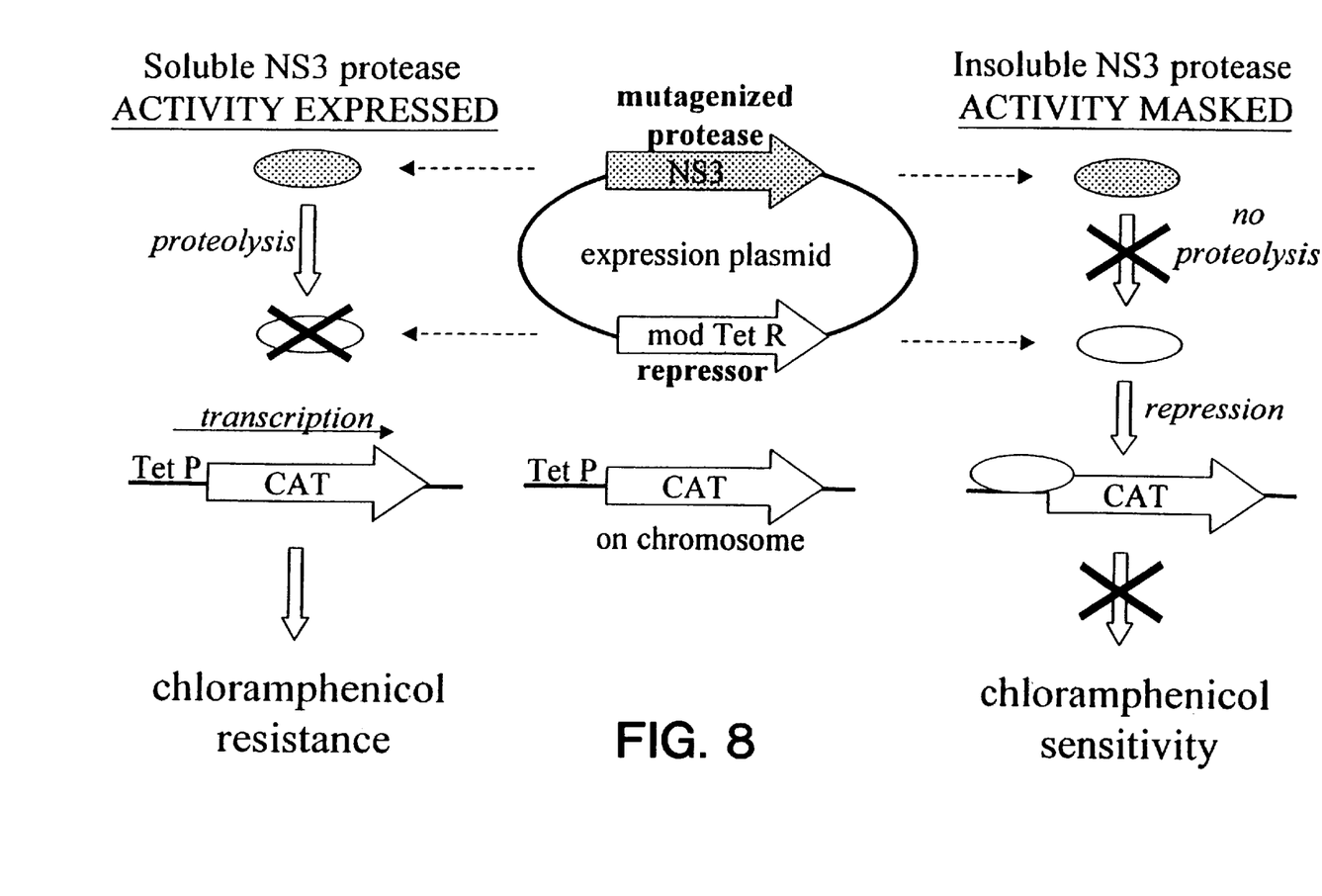
Figure 9:
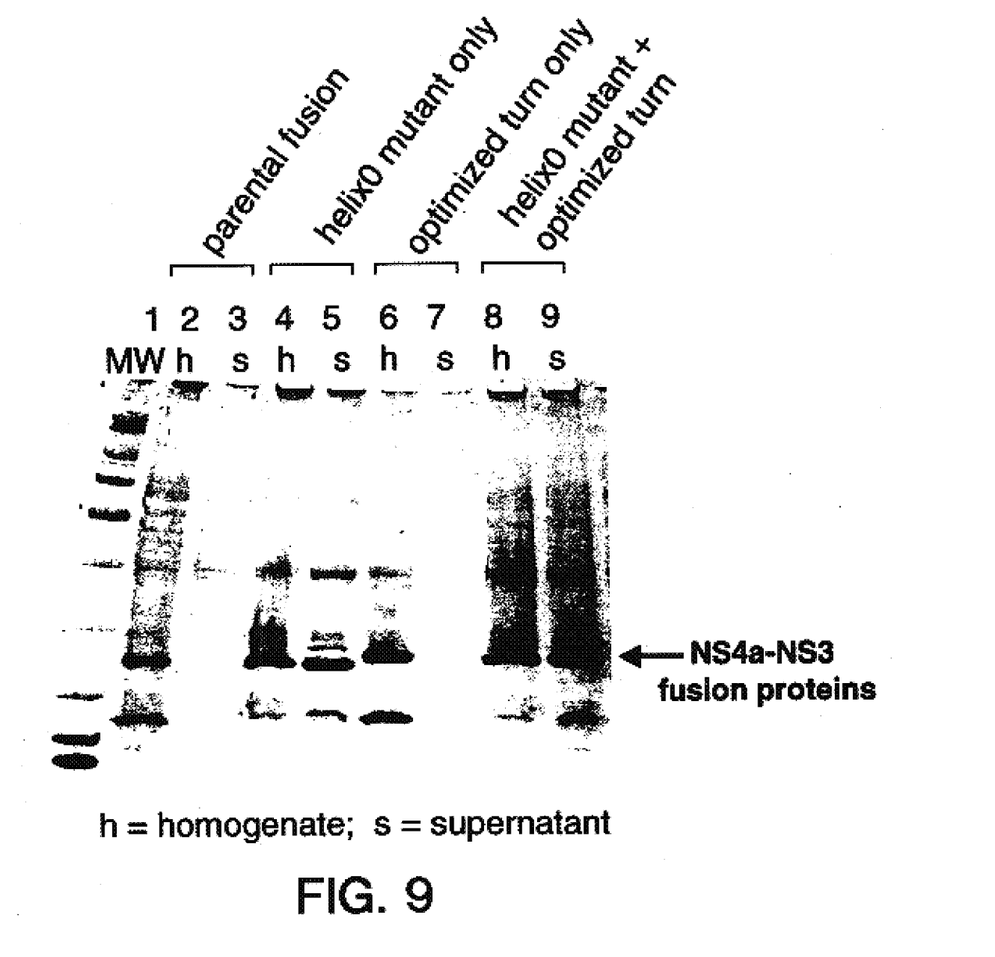

The activity of the hCMV protease in such a system can be easily monitored by measuring the ability of the strain to grow in the presence of chloramphenicol. Results of a typical experiment monitoring the induction of the protease using IPTG is as shown in the FIGS. 7 and 4.

Construction of the Expression Plasmid

The gene coding for the wild type tetracycline repressor including its own constitutive transcriptional promoter and ribosomal binding site was obtained from the commercially available plasmid pASK75. The gene was cloned into the plasmid vector, pUC18, using standard molecular biology techniques. Using site specific mutagenesis, NotI restriction enzyme cleavage sites were introduced into the DNA sequence of the tetracycline repressor right after the triplet coding for the amino acid residue #69 (after helix #4) and the triplet coding for the amino acid residue #155 (after helix #8) of the repressor. Again, using site-specific mutagenesis, DNA sequence for AscI restriction enzyme cleavage sites were introduced right after the triplet coding for the amino acid residue #72 (before helix #5) and the triplet coding for amino acid residue # 161 (before helix #9). During all of the manipulations, care was taken to maintain the reading frame of the tetracycline repressor. Thus, upon transcription and translation, a full-length tetracycline repressor was synthesized after the modifications. The insertion of these restriction enzyme cleavage sites into the DNA sequence of the tetracycline repressor gene had no effect on the ability of the modified tetracycline repressor to regulate transcription of a reporter gene from a tetracycline promoter.

The hCMV protease cleavage site was inserted using cassette mutagenesis. This was achieved by synthesizing two oligos, complementary to each other, comprising the DNA sequence coding for hCMV protease cleavage site and flanked by a NotI and an AscI site. The DNA sequence of the two oligo's are as given below:

Oligo 1: 5'-CCGGCGCGGCCGCGCCGCCGGGGGTCGT-
CAATGCCTCCTGCAGGCTCGCGAC-
CCCGCCGGGCGCGCCGGGGCCC-3'        (SEQ ID NO:9)

Oligo 2: 5'-GGGCCCCGGCGCGCCCGGCGGGGTCGC-
GAGCCTGCAGGAGGCATTGACGAC-
CCCCGGCGGCGCGGCCGCGCCGG-3'       SEQ ID NO: 10)

The two oligo's were mixed in an equi-molar ratio, annealed, and cut with the restriction enzymes NotI and AscI. Using standard molecular biology techniques, they were then inserted into the NotI and AscI sites engineered into the DNA sequence coding for the tetracycline repressor. During the design of the oligo's and all of the DNA manipulations, care was taken to maintain the reading frame of the tetracycline repressor. Again, upon transcription and translation, a full-length tetracycline repressor was synthesized containing the hCMV protease cleavage site. The insertion of the hCMV protease cleavage site had no adverse effect on the ability of the modified tetracycline repressor to regulate transcription of a reporter gene from a tetracycline repressor.

The gene coding for the hCMV protease was cloned first into a plasmid vector pET15. The sub-cloning was designed in such a manner that the expression of the hCMV protease gene was under the regulation of the T7 promoter. The entire cassette containing the T7 promoter, the ribosomal binding site and the gene coding for the hCMV protease was cloned into the above mentioned modified pUC18 plasmid vector containing the modified tetracycline repressor gene.

Figure 5:
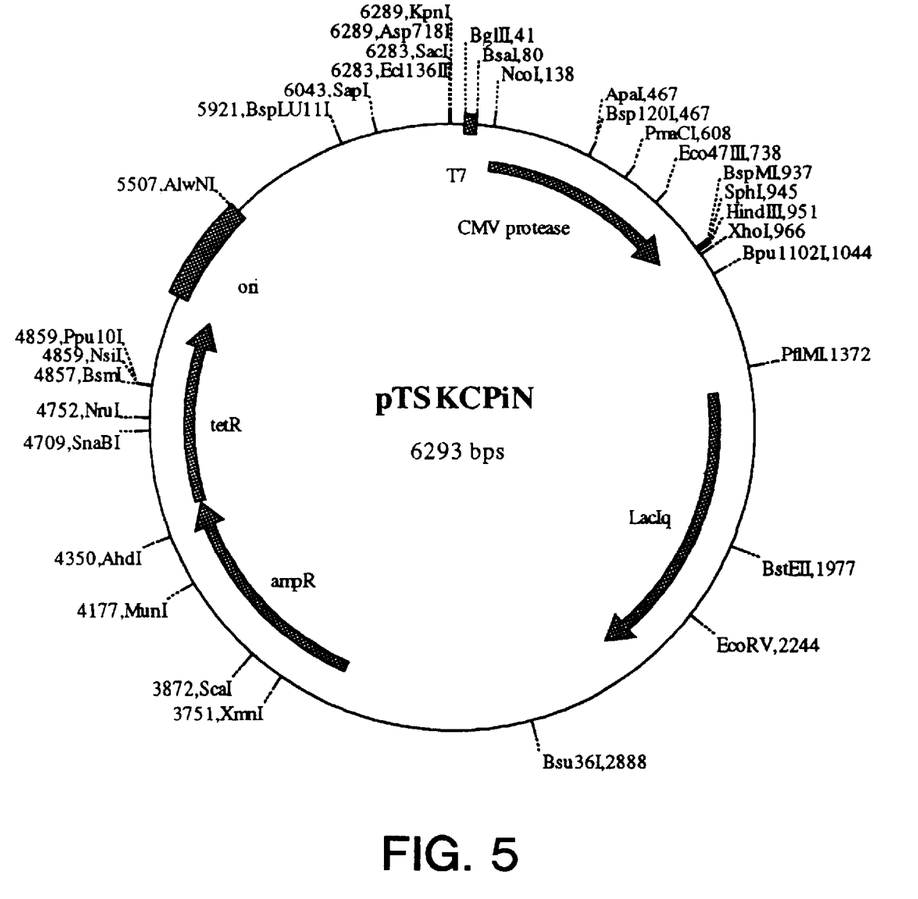

A schematic representation of the expression plasmid containing the hCMV protease gene and the modified tetracycline repressor containing the hCMV protease cleavage site is as shown in the FIG. 5.

A control expression plasmid was also constructed. The control expression plasmid was identical to the plasmid described above except the hCMV protease cleavage site was not inserted into the tetracycline repressor.

Construction of the Reporter Plasmid

Plasmid vector pMAK705, which contains a pSC101 temperature sensitive origin of replication and a gene conferring kanamycin resistance, was modified to contain a tetracycline promoter/operator system. This was achieved by inserting the DNA sequence containing i) a canonical *E. coli* promoter, ii) a tetracycline repressor binding site in between the −35 and the −10 region of the canonical promoter, iii) a tetracycline repressor binding site right after the +1 transcription start site and a HindIII restriction cleavage site. The insertion of the above module was done using cassette mutagenesis and standard molecular biology techniques. The DNA sequence of the module is as shown below:

5'-TTGACTCTATCATTGATAGAGTT-
TATAATGGATCCATCCCTATCAGTGATA-
GAGAGTCGACAAGCTT-3'         (SEQ ID NO: 11)

The CAT cartridge, containing the chloramphenicol acetyl-transferase gene and its own ribosomal binding site but not containing a transcriptional promoter was obtained as a cassette from Pharmacia Biotech Company. The cassette has HindIII site at either end for cloning purposes. The CAT cartridge was inserted into the HindIII site of the above mentioned modified plasmid vector pMAK705.

Development of Screening Strain

*E. coli* strain BL21(DE3) was obtained from Novagen Inc. This particular strain whose genotype is listed below has the ability to express genes under the regulation of the T7 promoter. The strain was transformed with the reporter plasmid and kanamycin resistant cells were isolated. Cells containing the reporter plasmid were then transformed either with the test or the control expression plasmid using ampicillin and kanamycin resistance as the selection for transformed cells. Genotype of BL21 (DE3): F-ompT[lon]hsdSB (rB-mB-) with DE3, a lambda prophage carrying the T7RNA polymerase gene.

Cells containing the reporter plasmid and the test expression plasmid were deposited with the American Type Culture Collection (ATCC), 10801 University Boulevard, Manassas, Va., 20110 USA, and have ATCC accession number 207047.

Suggested Screening Protocol for Protease Inhibitors

1) The screening strain containing the reporter plasmid and either the test expression plasmid or the control expression plasmid was inoculated into 30 ml of (LB+ Ampicillin 100 ug/ml and Kanamycin 15 ug/ml) in a 125 ml flask.
2) The culture was grown at 37° C. with shaking for 3–4 hours (OD 600 nm approx. 0.5 units) and then IPTG was added to the culture medium to a final concentration of 2.5 ug/ml. The culture was further incubated at 37° C. for and additional 1.5 hours.
3) The cultures were then used to seed LB molten agar (48° C.–50° C.)+ampicillin (100 ug/ml)+kanamycin (15 ug/ml)+chloramphenicol (3.5 ug/ml). The size of the innoculum used was 1%. The seeded molten agar was then poured into plates immediately (25 ml /100 mm diameter petri dish).
4) After the plates had cooled and solidified, depressions were made in the agar and test compounds were added to each depression. The compounds were allowed to diffuse into the agar for approximately 10–15 minutes and the plates were then incubated for 6–10 hours at 37° C. After incubation, any zones of growth inhibition observed were measured and compared.
5) Compounds that give a clear zone of growth inhibition for the strain containing the test expression plasmid as compared to the strain containing the control expression plasmid were deemed as positive hits. The positive hits can be confirmed in a second assay run exactly as described above except the addition chloramphenicol to the assay plates should be omitted. A true hit should not give a zone of growth inhibition under these conditions.

EXAMPLE 2

The system can be used to determine the cleavage site of a protease that has already been cloned and successfully expressed in a bacterial system in an active form. As in Example 1, described above, *E. coli* can be used as the organism to perform the assay. The tetracycline repressor can be used as the DNA-binding repressor molecule and the CAT reporter cartridge described above can be used as the reporter gene. As compared to that described in Example 1, instead of inserting the CMV protease cleavage site in between the amino acid proline (residue #69) and glycine (residue #72) of the tetracycline repressor, a random library of cleavage sites can be inserted.

The expression plasmid is constructed in a similar fashion as described above in Example 1. The protease for which its specific cleavage site needs to be determined can be cloned into the place of the CMV protease in the above mentioned expression plasmid using the NcoI and HindIII or any other appropriate restriction enzyme cleavage site.

Figure 6:
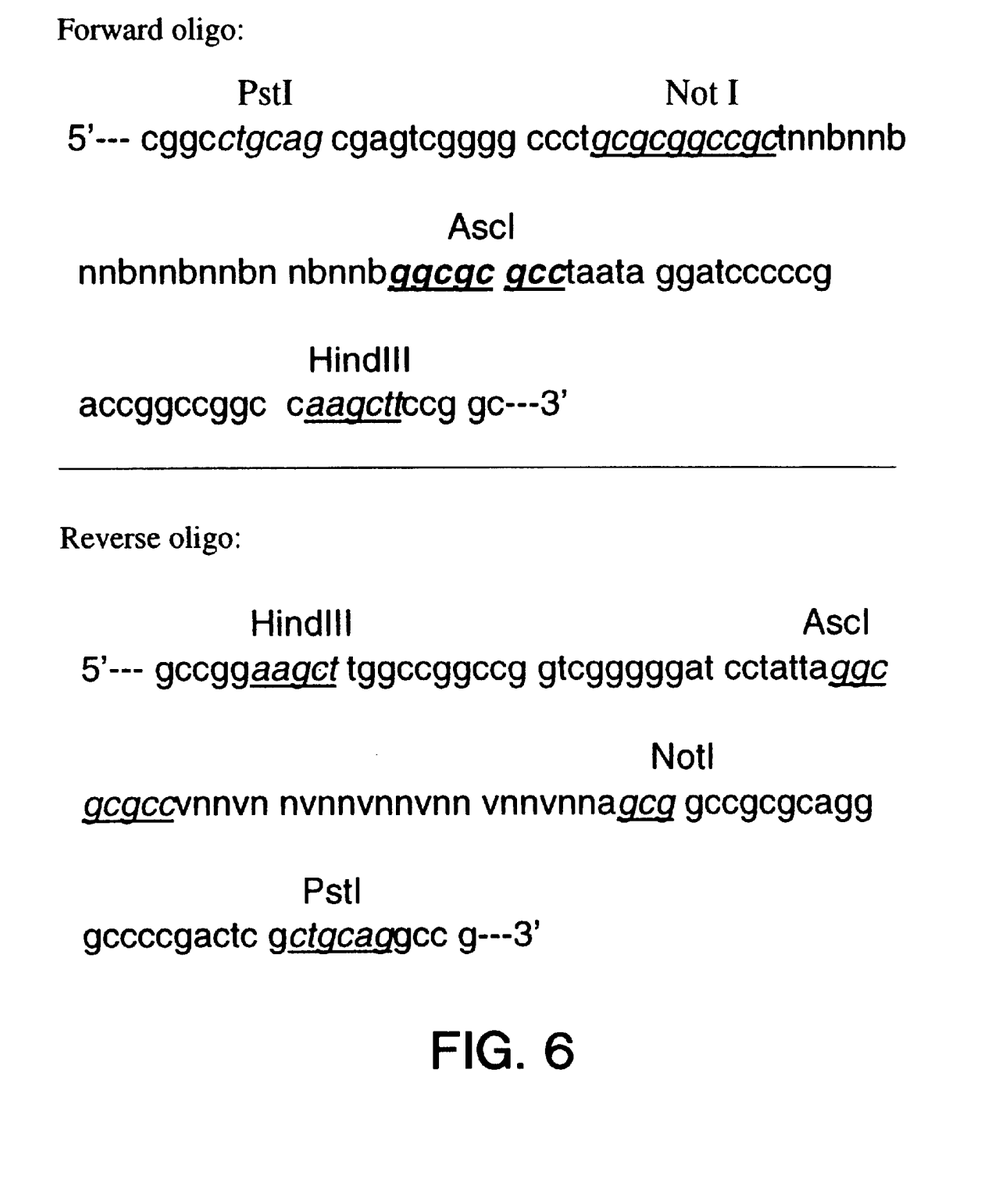
FIG. 6 is the DNA sequence of the forward (SEQ ID NO:5) and the reverse (SEQ ID NO:6) oligo used to generate the random library of cleavage sites. The relative positions of the relevant restriction enzyme sites are as shown. In the DNA sequence a=adenine, c=cytosine, t=thymidine, g=guanine, b=either g, t or c, v=either g, a or c and n=any of the four nucleotides.

The random library of cleavage sites can be constructed using standard molecular biological techniques. Briefly, random DNA oligo's are synthesized using the design as described in FIG. 6. The essential feature of the design of the random oligo's is that there is enough homology on either side of the random nucleotides to allow annealing with the formation of a "bubble" in between. The reverse and forward DNA oligo's need to be mixed in equi-molar concentration, annealed and cut with the restriction enzymes PstI and HindIII. The oligo's can then be ligated into the PstI and HindIII sites of an *E. coli* vector viz. pUC19. The ligation mixture can then be used to transform a mutS strain of *E. coli*. The mutS mutation does not repair the mis-match generated during the annealing of the two different oligos. The transformed culture should be allowed to recover for about an hour at 30° C. after transformation and then should be grown on selection media using the appropriate antibiotic. In the case of pUC19, one can use 100 ug/ml of ampicillin in Luria Broth. The cells should be grown in 500 ml of liquid media until stationery phase. The plasmid is then isolated from the culture. A large aliquot of the plasmid can then be cut with the restriction enzymes, NotI and AscI. The small fragment of DNA should be isolated. This isolated piece of DNA can then be ligated into the NotI and AscI sites of the expression plasmid described in above. Thus, one has now generated a random library of cleavage sites that have been inserted into an exposed and permissive loop of the tetracycline repressor has been generated.

As mentioned above, the same reporter cartridge as used in Example 1 can be used for this particular assay. The reporter plasmid can be constructed as described in Example 1.

Development of the *E. coli* Strain To Be Used for the Assay

E. colistrain BL21(DE3) (Novagen Inc.) or a similar strain which can allow expression from a T7 promoter can be used. The strain needs to be transformed with the reporter plasmid. The transformed cells can be selected using kanamycin resistance as the selection marker. Cells containing the reporter plasmid can then be transformed with the library of expression plasmid generated as described above. Resistance to ampicillin and kanamycin can be used to select for transformed cells. After the cells are transformed with both the plasmids, the library of expression plasmid and the reporter plasmid, the cells need to be grown for several generations (stationery phase) in 100 ml liquid Luria Broth under antibiotic selection pressure. The cells then need to be stored in a frozen state in 2-ml aliquots. Genotype of BL21(DE3): F-ompT[lon]hsdSB(rB-mB-) with DE3, a lambda prophage carrying the T7RNA polymerase gene.

Suggested Screening Protocol for Identification of Specific Cleavage Site

1) A vial of frozen *E. coli* cells described above which contain the reporter plasmid and an expression plasmid out of the library of expression plasmids should be thawed gently on ice.
2) Several petri dish (100 mm diameter each) containing rich medium and supplemented with ampicillin (100 ug/ml)+ kanamycin (15 ug/ml)+chloramphenicol (15 ug/ml)+ IPTG (20 ug/ml) should be plated using a 100 uL aliquot of the above-mentioned thawed *E. coli* culture.
3) The plates should be incubated at 30° C. over-night. Colonies obtained after over-night incubation should be tested again for chloramphenicol resistance by growing the cells in the presence of 15-ug/ml chloramphenicol.
4) The expression plasmid from each of the chloramphenicol resistant colony should be isolated individually. The DNA sequence of the modified tetracycline repressor should be determined and the amino acid sequence of the cleavage site should then be deduced from the DNA sequence.
5) The amino acid sequence of the cleavage site should then be confirmed using a secondary assay viz. as cleavage of a synthetically generated substrate.

EXAMPLE 3

The systems can be used to clone a protease whose specific cleavage site is known. As in Example 1, described above, *E. coli* can be used as the organism to perform the assay. The tetracycline repressor can be used as the DNA-binding repressor molecule and the CAT reporter cartridge described above can be used as the reporter gene. As compared to that described in Example 1, instead of inserting the CMV protease cleavage site in between the amino acid proline (residue #69) and glycine (residue #72) of the tetracycline repressor, the specific cleavage site should be inserted.

First, a plasmid based expression library using the genomic DNA or cDNA obtained from the organism from which the protease needs to be cloned is constructed using standard molecular biological techniques. The gene coding for the tetracycline repressor is modified to contain the appropriate specific cleavage site as described in Example 1. The gene coding for the modified tetracycline repressor containing its own promoter and ribosomal binding site is sub-cloned into the above mentioned plasmid based expression library. Thus, it is similar to the expression plasmid described in Example 1, except that tetracycline repressor contains the appropriate cleavage site as opposed to the hCMV protease cleavage site, and, a genomic or cDNA library is substituted instead of the hCMV protease gene.

As mentioned above, the same reporter cartridge as used in Example 1 can be used for this particular assay. The reporter plasmid can be constructed as described in Example 1.

Development of the *E. coli* Strain To Be Used for the Assay

An *E. coli* strain, which is compatible with the plasmid based expression library described above can be used. The strain needs to be transformed with the reporter plasmid. The transformed cells can be selected using kanamycin resistance as the selection marker. Cells containing the reporter plasmid can then be transformed with the library of expression plasmid generated as described above. Resistance to the appropriate antibiotics can be used to select for transformed cells. After the cells are transformed with both the plasmids, the library of expression plasmid and the reporter plasmid, the cells need to be grown for several generations (stationery phase) in 100 ml liquid Luria Broth under antibiotic selection pressure. The cells then need to be stored in a frozen state in 2-ml aliquots.

Suggested Screening Protocol for Cloning of the Protease Gene

1) A vial of frozen *E. coli* cells described above which contain the reporter plasmid and an expression plasmid out of the library of expression plasmids should be thawed gently on ice.
2) Several petri dish (100 mm diameter) containing rich medium and supplemented with ampicillin (100 ug/ml)+ kanamycin (15 ug/ml)+chloramphenicol (15 ug/ml)+ IPTG (20 ug/ml) should be plated using a 100 uL aliquot of the above-mentioned thawed *E. coli* culture.

3) The plates should be incubated at 30° C. over-night. Colonies obtained after over-night incubation should be tested again for chloramphenicol resistance by growing the cells in the presence of 15-ug/ml chloramphenicol.

4) The expression plasmid from each of the chloramphenicol resistant colonies should be isolated individually. The DNA sequence of the genomic or cDNA fragment insert should be determined.

5) The proteolytic activity produced from the fragment of the genomic or cDNA insert should then be further confirmed using a secondary assay viz. as cleavage of a synthetic substrate (radiolabeled, fluorogenic or ELISA) using appropriate detection methods.

6) If an entire open reading frame is not obtained, the cloned protease fragment can be used to clone the entire gene using standard hybridization techniques.

EXAMPLE 4

Wild type hepatitis C virus (HCV) NS3 protease is insoluble when expressed in *E. coli* and thus has limited use for research purposes. In vivo, the HCV NS4a protein stimulates HCV NS3 protease activity through the formation of a heteromeric complex with HCV NS3. A library of mutant HCV NS4a-NS3 fusion proteases was made to find mutants that expressed a soluble and active protease.

In the case of HCV, the expressed wild type HCV protease is inherently active; however, the activity is masked by the insoluble character of the expressed protease, resulting in a chloramphenicol sensitive ($Cm^S$) phenotype. If among the pool of mutants a more soluble active mutant protease is expressed, the inherent activity of the protease is unmasked by the soluble nature of the mutant enzyme and the cells harboring this mutant protease become chloramphenicol resistant ($Cm^R$).

The present invention was used to screen a library of mutant HCV NS4a-NS3 fusion proteases for mutants that expressed a soluble and active protease. The bacterial selection system is diagramed in FIG. 8. The system differs from that described with CMV in Example 1 in that the plasmid containing the Tet repressor has a HCV cleavage site within the Tet repressor (rather than a CMV cleavage site) and contains an HCV protease (rather than a CMV protease), and in that the CAT gene is on the chromosome (rather than on a second plasmid). One of ordinary skill in the art could make the system using HCV from the system using CMV using standard techniques of molecular biology.

The system features a plasmid encoding a mutagenized HCV NS4a-NS3 protease gene as well as a gene encoding a modified Tet repressor. The modification of the Tet repressor is the introduction of a HCV NS3 protease cleavage site within a solvent-exposed loop of the Tet repressor protein. The strain carrying this plasmid also has a chromosomally-encoded chloramphenicol acetylase transferase gene (CAT-conferring chloramphenicol resistance) under the control of the Tet promoter. After induction of the mutant HCV NS4a-NS3 fusion protease by IPTG (under lac-T7 control), the strain becomes either chloramphenicol resistant ($Cm^R$) if the protease activity is present (because cleavage of the modified Tet repressor allows expression of CAT), or remains chloramphenicol sensitive ($Cm^S$) if fusion protease activity is not present (because there is no cleavage of the modified Tet repressor and therefore there is repression of CAT).

Expression of a unmutagenized HCV NS4a-NS3 fusion protease (having wild type HCV NS4a and NS3 sequence) in this system yielded *E.coli* cells that grew only very slowly on agar plates with 1 μg/ml chloramphenicol. The library of mutant HCV NS4a-NS3 fusion proteases was transformed into the *E.coli* selection strain. Many plasmids encoding mutant HCV NS4a-NS3 fusion proteases conferred upon induced transformed *E.coli* cells an enhanced ability to grow on plates with low levels of chloramphenicol (1–3 μg/ml chloramphenicol). However, twelve transformants grew on plates with very high levels of chloramphenicol (30 μg/ml). These highly $Cm^R$ transformants were colony purified and solubilities of the mutant HCV NS4a-NS3 fusion proteases were evaluated by SDS-PAGE analysis (similar to that depicted in FIG. 9). Six of the transformants exhibited more soluble proteases than the others, and plasmid DNA was prepared and sequenced.

FIG. 9 (lanes 4 and 5) show one such mutant HCV NS4a-NS3 fusion protease in the soluble fraction, while a unmutagenized fusion protease was insoluble (lanes 2 and 3). Similar results were obtained with the other five mutant HCV NS4a-NS3 fusion protease (data not shown).

This example describes using the present invention to screen protease mutants for solubility which leads to unmasked activity. The present invention could similarly be used to screen various wild type isolates for activity. The activity could be due to solubility of a naturally-occurring variant form of the protease or could be due to inherent activity of the naturally-occurring variant.

The production of mutant HCV NS4a-NS3 fusion proteases referred to herein is further described in copending applications U.S. Serial No. 60/115,271, filed Jan. 8, 1999, and U.S. Ser. No. 09/478,479, Now U.S. Pat. No. 6,333,186, filed on even date herewith, both of which are incorporated herein by reference.

What is claimed is:

1. A prokaryotic cell system for monitoring protease activity comprising a prokaryotic cell comprising:
   (a) a gene coding for a protease;
   (b) a gene encoding a modified DNA-binding repressor wherein the modification of the repressor comprises two cognate cleavage sites of the protease of (a) engineered into regions of the repressor such that the repressor's DNA binding activity to its cognate DNA sequence is not destroyed yet the cognate cleavage site is accessible to the protease; and
   (c) a reporter cartridge wherein the expression of the reporter gene in the cartridge is regulated by a promoter whose transcription can be negatively regulated by the wild type repressor corresponding to the modified DNA-binding repressor or by the modified DNA-binding repressor.

2. The prokaryotic cell system of claim 1 wherein said prokaryotic cell is *E. coli*.

3. The prokaryotic cell system of claim 1 further comprising an inducible promoter that can regulate said gene coding for the protease.

4. The prokaryotic cell system of claim 3, wherein said inducible promoter that can regulate said gene coding for the protease is the lac promoter.

5. The prokaryotic cell system of claim 1 wherein transcription of said gene encoding a modified DNA-binding repressor is constitutively active.

6. The prokaryotic cell system of claim 1 wherein said modified DNA-binding repressor is a modified tetracycline repressor.

7. The prokaryotic cell system of claim 6 wherein the constitutive transcriptional promoter of the tetracycline repressor gene is operatively linked to the sequence encoding the modified tetracycline repressor.

8. The prokaryotic cell system of claim 1 wherein said reporter gene is a chloramphenicol acetyl transferase (CAT) gene.

9. The prokaryotic cell system of claim 8 wherein said gene encoding a modified DNA-binding repressor is a gene encoding a modified tetracycline repressor, and further comprising a tetracycline promoter wherein said CAT gene is regulated by the interaction of said modified tetracycline repressor with said tetracycline promoter.

10. The prokaryotic cell system of claim 1 wherein each of (a), (b) and (c) are on a plasmid.

11. The prokaryotic cell system of claim 1 wherein each of (a) and (b) are on a plasmid and (c) is on the chromosome.

12. The prokaryotic cell system of claim 9 wherein said protease is a human cytomegalovirus (hCMV) protease.

13. A cell as defined by ATCC culture accession number 207047.

14. A prokaryotic cell system for monitoring protease activity comprising a prokaryotic cell comprising:
  (a) a gene coding for a protease;
  (b) a gene encoding a modified DNA-binding repressor wherein the modification of the repressor comprises one or more cognate cleavage sites of the protease of (a) engineered between helices 4 and 5 or between helices 8 and 9 of the repressor; and
  (c) a reporter cartridge wherein the expression of the reporter gene in the cartridge is regulated by a promoter whose transcription can be negatively regulated by the wild type repressor corresponding to the modified DNA-binding repressor or by the modified DNA-binding repressor;
  wherein said modified DNA-binding repressor is a modified tetracycline repressor.

15. The prokaryotic cell system of claim 14 wherein a cognate cleavage site of the protease is engineered both between helices 4 and 5 and between helices 8 and 9 of the repressor.

16. A prokaryotic cell system for monitoring protease activity comprising a prokaryotic cell comprising:
  (a) a gene coding for a protease;
  (b) a gene encoding a modified DNA-binding repressor wherein the modification of the repressor comprises one or more cognate cleavage sites of the protease of (a) engineered into the repressor, wherein at least one cognate cleavage site of the protease is engineered into the region between the helices forming the DNA-binding domain and the helices responsible for dimer formation; and
  (c) a reporter cartridge wherein the expression of the reporter gene in the cartridge is regulated by a promoter whose transcription can be negatively regulated by the wild type repressor corresponding to the modified DNA-binding repressor or by the modified DNA-binding repressor;
  wherein said modified DNA-binding repressor is a modified tetracycline repressor.

17. A prokaryotic cell system for monitoring protease activity comprising a prokaryotic cell comprising:
  (a) a gene coding for a protease;
  (b) a gene encoding a modified DNA-binding repressor wherein the modification of the repressor comprises one or more cognate cleavage sites of the protease of (a) engineered between helices of the repressor responsible for dimer formation of the repressor; and
  (c) a reporter cartridge wherein the expression of the reporter gene in the cartridge is regulated by a promoter whose transcription can be negatively regulated by the wild type repressor corresponding to the modified DNA-binding repressor or by the modified DNA-binding repressor;
  wherein said modified DNA-binding repressor is a modified tetracycline repressor.

18. The prokaryotic cell system of claim 17 wherein the modified repressor further comprises a cognate cleavage site that is not engineered between helices responsible for dimer formation of the repressor.

19. The prokaryotic cell system of claim 16 wherein said reporter gene is a chloramphenicol acetyl transferase (CAT) gene.

20. The prokaryotic cell system of claim 17 wherein said reporter gene is a chloramphenicol acetyl transferase (CAT) gene.

21. The prokaryotic cell system of claim 1 wherein said modified DNA-binding repressor occurs as a homo-dimer with an alpha helix-turn alpha helix motif.

22. The prokaryotic cell system of claim 17, wherein the modification of the repressor further comprises one or more cognate cleavage sites of the protease engineered into the region between the helices forming the DNA-binding domain and the helices responsible for dimer formation.

23. The prokaryotic cell system of claim 17, wherein the modification of the repressor consists of cognate cleavage sites of the protease engineered between helices responsible for dimer formation, and into the region between the helices forming the DNA-binding domain and the helices responsible for dimer formation.

24. The prokaryotic cell system of claim 15, wherein a cognate cleavage site is engineered into the repressor between the proline at residue 5 and the glycine at residue 8 according to SEQ ID NO: 1, and a cognate cleavage site is engineered between the lysine at residue 3 and the proline at residue 9 according to SEQ ID NO: 3.

* * * * *

SEQUENCE LISTING

```
<160> NUMBER OF SEQ ID NOS:  11

<210> SEQ ID NO 1
<211> LENGTH: 11
<212> TYPE: PRT
<213> ORGANISM: Escherichia coli

<400> SEQUENCE: 1

His Thr Phe Cys Pro Leu Glu Gly Glu Ser Trp
```

```
                          1               5                        10
```

<210> SEQ ID NO 2
<211> LENGTH: 15
<212> TYPE: PRT
<213> ORGANISM: human cytomegalorivus

<400> SEQUENCE: 2

Ala Ala Ala Gly Val Val Asn Ala Ser Cys Arg Leu Gly Ala Pro
 1               5                  10                  15

<210> SEQ ID NO 3
<211> LENGTH: 16
<212> TYPE: PRT
<213> ORGANISM: Escherichia coli

<400> SEQUENCE: 3

Val Ala Lys Glu Glu Arg Glu Thr Pro Thr Thr Asp Ser Met Pro Pro
 1               5                  10                  15

<210> SEQ ID NO 4
<211> LENGTH: 14
<212> TYPE: PRT
<213> ORGANISM: human cytomegalovirus

<400> SEQUENCE: 4

Ala Ala Ala Gly Val Val Asn Ala Ser Cys Arg Leu Gly Ala
 1               5                  10

<210> SEQ ID NO 5
<211> LENGTH: 101
<212> TYPE: DNA
<213> ORGANISM: Artificial Sequence
<220> FEATURE:
<221> NAME/KEY: misc_feature
<222> LOCATION: (36)..(55)
<223> OTHER INFORMATION: n = adenine, cytosine, thymidine or guanine
<221> NAME/KEY: misc_feature
<222> LOCATION: (38)..(56)
<223> OTHER INFORMATION: b = guanine, thymidine or cytosine
<223> OTHER INFORMATION: Description of Artificial Sequence:
      oligonucleotide used to generate random library of cleavage sites

<400> SEQUENCE: 5
cggcctgcag cgagtcgggg ccctgcgcgg ccgctnnbnn bnnbnnbnnb nnbnnbggcg        60
cgcctaatag gatcccccga ccggccggcc aagcttccgg c                          101

<210> SEQ ID NO 6
<211> LENGTH: 101
<212> TYPE: DNA
<213> ORGANISM: Artificial Sequence
<220> FEATURE:
<221> NAME/KEY: misc_feature
<222> LOCATION: (46)..(64)
<223> OTHER INFORMATION: v = guanine, adenine or cytosine
<221> NAME/KEY: misc_feature
<222> LOCATION: (47)..(66)
<223> OTHER INFORMATION: n = adenine, cytosine, thymidine or guanine
<223> OTHER INFORMATION: Description of Artificial Sequence:
      oligonucleotide used to generate random library of cleavage sites

<400> SEQUENCE: 6
gccggaagct tggccggccg gtcgggggat cctattaggc gcgccvnnvn nvnnvnnvnn        60
vnnvnnagcg gccgcgcagg gccccgactc gctgcaggcc g                          101

<210> SEQ ID NO 7

-continued

```
<211> LENGTH: 17
<212> TYPE: DNA
<213> ORGANISM: Escherichia coli
<220> FEATURE:
<221> NAME/KEY: misc_feature
<222> LOCATION: (2)..(16)
<223> OTHER INFORMATION: n = adenine, cytosine, thymidine or guanine

<400> SEQUENCE: 7
cnctatcant gatagng                                                    17

<210> SEQ ID NO 8
<211> LENGTH: 12
<212> TYPE: PRT
<213> ORGANISM: human cytomegalovirus

<400> SEQUENCE: 8

Ala Gly Val Val Asn Ala Ser Cys Arg Leu Gly Ala
 1               5                  10

<210> SEQ ID NO 9
<211> LENGTH: 74
<212> TYPE: DNA
<213> ORGANISM: human cytomegalovirus

<400> SEQUENCE: 9
ccggcgcggc cgcgccgccg ggggtcgtca atgcctcctg caggctcgcg accccgccgg     60
gcgcgccggg gccc                                                      74

<210> SEQ ID NO 10
<211> LENGTH: 74
<212> TYPE: DNA
<213> ORGANISM: human cytomegalovirus

<400> SEQUENCE: 10
gggccccggc gcgcccggcg gggtcgcgag cctgcaggag gcattgacga ccccggcgg     60 cgcggccgcg ccgg                                                      74

<210> SEQ ID NO 11
<211> LENGTH: 67
<212> TYPE: DNA
<213> ORGANISM: Artificial Sequence
<220> FEATURE:
<223> OTHER INFORMATION: Description of Artificial Sequence:Escherichia
      coli promoter and Escherichia coli tetracycline
      repressor binding sites

<400> SEQUENCE: 11
ttgactctat cattgataga gtttataatg gatccatccc tatcagtgat agagagtcga    60
caagctt                                                              67
```